United States Patent
Hatcher, Jr. et al.

(10) Patent No.: US 9,681,107 B2
(45) Date of Patent: Jun. 13, 2017

(54) FLEXIBLE TETHER POSITION TRACKING CAMERA INSPECTION SYSTEM FOR VISUAL INSPECTION OF OFF LINE INDUSTRIAL GAS TURBINES AND OTHER POWER GENERATION MACHINERY

(71) Applicant: SIEMENS ENERGY, INC., Orlando, FL (US)

(72) Inventors: Clifford Hatcher, Jr., Orlando, FL (US); Forrest R. Ruhge, Orlando, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 333 days.

(21) Appl. No.: 14/284,437

(22) Filed: May 22, 2014

(65) Prior Publication Data

US 2015/0341600 A1 Nov. 26, 2015

(51) Int. Cl.
*H04N 7/18* (2006.01)
*H04N 5/225* (2006.01)
*F01D 21/00* (2006.01)
*G02B 23/24* (2006.01)
*G01N 21/954* (2006.01)

(52) U.S. Cl.
CPC ........... *H04N 7/183* (2013.01); *F01D 21/003* (2013.01); *G01N 21/954* (2013.01); *G02B 23/2476* (2013.01); *G02B 23/2484* (2013.01); *H04N 5/2251* (2013.01); *H04N 2005/2255* (2013.01)

(58) Field of Classification Search
None
See application file for complete search history.

(56) References Cited

U.S. PATENT DOCUMENTS

| 5,164,826 A | 11/1992 | Dailey |
| 5,349,850 A | 9/1994 | Young |
| 6,101,455 A * | 8/2000 | Davis ................ B25J 9/1697 382/153 |
| 6,387,002 B1 | 5/2002 | Gunter |
| 6,728,582 B1 * | 4/2004 | Wallack ........... G05B 19/41875 382/153 |
| 6,992,315 B2 | 1/2006 | Twerdochlib |
| 7,068,029 B2 | 6/2006 | Hatcher et al. |

(Continued)

FOREIGN PATENT DOCUMENTS

| DE | 3504824 | 8/1986 |
| EP | 0907077 | 4/1999 |

(Continued)

OTHER PUBLICATIONS

Energy Chain System E2 Tubes Series R09, pp. 5.13-5.16, RoHS info: www.igus.com/RoHS, www.igus.com/e-chain-pdfs. Cited as exemplary of known energy chain structure.

*Primary Examiner* — Mohammad J Rahman (57) ABSTRACT

A camera scope inspection system with a flexible, tether mounted camera head that is maneuverable in confined internal cavities of power generation machinery. A camera head position sensing system inferentially determines the three dimension (3D) position of the camera head within the inspected machinery. Camera head position data are correlated with camera image data by a controller. In this manner correlated internal inspection image data and corresponding position data are available for future analysis and image tracking.

17 Claims, 4 Drawing Sheets

(56) References Cited

U.S. PATENT DOCUMENTS

| | | |
|---|---|---|
| 7,489,811 B2 | 2/2009 | Brummel et al. |
| 8,378,691 B2 | 2/2013 | Moser et al. |
| 8,892,252 B1 * | 11/2014 | Troy ............... G01B 11/14 |
| | | 700/213 |
| 2004/0051525 A1 | 3/2004 | Hatcher et al. |
| 2004/0176683 A1 * | 9/2004 | Whitin ............... A61B 5/06 |
| | | 600/424 |
| 2005/0199832 A1 | 9/2005 | Twerdochlib |
| 2006/0030771 A1 * | 2/2006 | Levine ............... A61B 5/06 |
| | | 600/424 |
| 2006/0033908 A1 * | 2/2006 | Draggie ......... G02B 23/2476 |
| | | 356/241.4 |
| 2006/0088793 A1 | 4/2006 | Brummel et al. |
| 2007/0129604 A1 | 6/2007 | Hatcher et al. |
| 2007/0157733 A1 | 7/2007 | Litzenberg et al. |
| 2007/0225550 A1 * | 9/2007 | Gattani ............... A61B 90/36 |
| | | 600/101 |
| 2007/0296964 A1 | 12/2007 | Nishimura |
| 2008/0287741 A1 | 11/2008 | Ostrovsky et al. |
| 2008/0319557 A1 * | 12/2008 | Summers ......... G05B 19/4015 |
| | | 700/19 |
| 2009/0089020 A1 * | 4/2009 | Boyer ............... F01D 25/285 |
| | | 703/1 |
| 2009/0304374 A1 * | 12/2009 | Fruehauf ............ G01S 5/0284 |
| | | 396/153 |
| 2010/0113876 A1 * | 5/2010 | Ishihara ........... A61B 1/00147 |
| | | 600/117 |
| 2011/0018530 A1 | 1/2011 | Bousquet et al. |
| 2011/0109898 A1 | 5/2011 | Froggatt et al. |
| 2011/0306831 A1 | 12/2011 | Kohnke et al. |
| 2012/0281084 A1 * | 11/2012 | Hatcher ............... F01D 9/023 |
| | | 348/83 |
| 2013/0188018 A1 * | 7/2013 | Stevens ............... G06T 7/0004 |
| | | 348/46 |
| 2013/0192353 A1 | 8/2013 | Hatcher, Jr. |
| 2013/0194413 A1 | 8/2013 | Hatcher et al. |
| 2013/0335530 A1 | 12/2013 | Hatcher, Jr. |
| 2014/0055596 A1 | 2/2014 | Hatcher, Jr. |

FOREIGN PATENT DOCUMENTS

| | | | |
|---|---|---|---|
| GB | 2493770 A | * 2/2013 | ......... G02B 23/2476 |
| WO | 96/17695 | 6/1996 | |
| WO | 2011042744 | 4/2011 | |

\* cited by examiner

FLEXIBLE TETHER POSITION TRACKING CAMERA INSPECTION SYSTEM FOR VISUAL INSPECTION OF OFF LINE INDUSTRIAL GAS TURBINES AND OTHER POWER GENERATION MACHINERY

CROSS-REFERENCE TO RELATED APPLICATIONS

This application incorporates by reference the entire contents of each of co-pending U.S. patent applications:

"Flexible Linkage Camera System And Method For Visual Inspection Of Off Line Industrial Gas Turbines And Other Power Generation Machinery", filed Aug. 21, 2013, Ser. No. 13/972,332, United States patent application publication number 2014/0055596;

"System And Method For Visual Inspection And 3D White Light Scanning Of Off-Line Industrial Gas Turbines And Other Power Generation Machinery", filed Aug. 21, 2013, Ser. No. 13/97,200, United States patent application publication number 2013/0335530; and "System And Method For Automated Optical Inspection Of Industrial Gas Turbines And Other Power Generation Machinery With Multi-Axis Inspection Scope", filed Jan. 31, 2012, Ser. No. 13/362,352, United States patent application publication number 2013/0192353.

BACKGROUND OF THE INVENTION

1. Field of the Invention

The invention relates to optical camera systems for non-destructive internal inspection of power generation machinery, including by way of non-limiting example industrial gas and steam turbine engines as well as generators. More particularly aspects of the invention relate to a visible light or infra-red optical camera inspection system that is capable of positioning camera fields of view (FOV) through a gas turbine inspection port, inlet or outlet in any portion of the engine, including the compressor section, combustor nozzle and transition and turbine section, capturing visual images of the engine's internal structure. One or more cameras are mounted within a camera head that is translated to areas of interest within the turbine or other power generation machinery by a flexible tether, so that their respective fields of view capture desired images. The includes a camera head position system that inferentially determines three dimension (3D) position of the camera head, so that the captured images and their position are correlated for future analysis. In this manner images from any inspected position within the machinery can be selectively recalled for review or multiple images can be stitched to create a composite image of the machinery inspected areas.

2. Description of the Prior Art

Power generation machinery, such as steam or gas industrial turbines, are often operated continuously with scheduled inspection and maintenance periods, at which time the turbine is taken offline and shut down. By way of example, a gas turbine engine often will be operated to generate power continuously for approximately 4000 hours, thereupon it is taken off line for routine maintenance, inspection, and repair of any components identified during inspection. Taking a gas turbine off line and eventually shutting it down completely for scheduled maintenance is a multi-day project. Some turbine components, such as the turbine rotor section, are operated at temperatures exceeding 1000° C. (1832° F.). The turbine requires 48-72 hours of cooling time to achieve ambient temperature before complete shutdown in order to reduce likelihood of component warping or other deformation. During the shutdown phase the turbine rotor rotational speed is spooled down from operating speed of approximately 3600 RPM to a speed of approximately 120 RPM or less in "turning gear mode" where the rotor is externally driven by an auxiliary drive motor, in order to reduce likelihood of rotor warping. Other turbine components, such as the turbine housing, are also cooled slowly to ambient temperature.

Once the turbine is cooled to ambient temperature over the course of up to approximately 72 hours internal components of the now static turbine can be inspected with optical camera inspection systems. Known optical camera inspection systems employ rigid or flexible optical bore scopes that are inserted into inspection ports located about the turbine periphery. The bore scope is manually positioned so that its field of view encompasses an area of interest within the turbine, such as one or more vanes or blades, combustor baskets, etc. A camera optically coupled to the bore scope captures images of objects of interest within the field of view for remote visualization and archiving (if desired) by an inspector.

If a series of different images of different areas of interest within a given turbine inspection port are desired, the inspector must manually re-position the camera inspection system bore scope to achieve the desired relative alignment of internal area of interest and the field of view. Relative alignment can be achieved by physically moving the bore scope so that its viewing port is positioned proximal a static area of interest. Examples of such relative movement of bore scope and static turbine component are by inserting a bore scope in different orientations within a static combustor or radially in and out of space between a vane and blade row within the compressor or turbine sections. For rotating blade inspection, relative alignment can also be achieved by maintaining the bore scope viewing port in a static position and rotating the blade row blades successively into the camera static viewing field.

Previously referenced, commonly owned United States publication number 2013/0335530, entitled "System And Method For Visual Inspection And 3D White Light Scanning Of Off-Line Industrial Gas Turbines And Other Power Generation Machinery" and United States patent application publication number 2013/0192353, entitled "System And Method For Automated Optical Inspection Of Industrial Gas Turbines And Other Power Generation Machinery With Multi-Axis Inspection Scope" describes motorized inspection system embodiments that can be automatically maneuvered within power generation machinery or manually maneuvered under control of a human operator. Relative orientation coordinates of the driven motion axes are monitored by the system, so that the inspection camera head position and orientation are known by referencing those axes coordinates.

In other types of power generation machinery internal optical inspection procedures it is desirable to position manually under human operator control a camera head mounted on a flexible tether and record the camera images, as is described in previously referenced, commonly owned United States publication number 2014/0055596, entitled "Flexible Linkage Camera System And Method For Visual Inspection Of Off Line Industrial Gas Turbines And Other Power Generation Machinery". For example, non-rotating static vane inspections within compressor or turbine section rows require physical movement of the inspection scope camera system field of view to each individual vane. The narrow confines of passages surrounding stationary vanes often will not facilitate passage of traditional inspection scope systems. In order to complete inspection of the vanes, supporting structures, such as vane shrouds are removed to provide sufficient visual exposure and/or passage of inspection scope components within the restricted confines of vane rows.

Thus, complete turbine inspection with a flexible, tethered camera inspection system, such as that described in United States publication number 2014/0055596, requires multiple manual relative repositioning sequences between the camera inspection system viewing ports and other internal inspection access points to allow complete visual inspection of all areas of interest within the turbine. Inspection apparatus positioning is challenging due to the complex, often tortuous manipulation paths between components in a gas turbine. The inspection scope camera delivery system must be sufficiently flexible to insert through tight confined passages, yet not too flexible or limp to prevent controlled positioning within the passages. Unlike the aforementioned motorized multi-axis inspection system that is described in United States patent application publication number 2013/0192353, the flexible tethered camera inspection system does not provide camera head position/orientation information that can be advantageously combined with the optical image information for future analysis or composite image generation.

SUMMARY OF THE INVENTION

Accordingly, a suggested object of the invention is to correlate flexible tethered camera inspection system camera head position with captured images, such as is possible with a motorized multi-axis camera inspection system.

This and other objects are achieved in one or more embodiments of the invention by a camera scope inspection system with a flexible tether mounted camera head and a camera head position sensing system that inferentially determines the three dimension (3D) position of the camera head. Camera head position data are correlated with camera image data by a controller. In this manner correlated internal inspection image data and corresponding position data are available for future analysis and image tracking similar to data processing performed with data gathered from multi-axis motorized inspection systems, with the advantages of being able to maneuver manually the tethered camera scope into confined spaces not readily accessible by the multi-axis systems.

Some embodiments of the invention feature a flexible, position tracking camera scope inspection system for internal inspection of power generation machinery. The system includes a camera scope with a flexible elongated tether, having a distal end adapted for insertion into a blind cavity of a rotating machine. A camera head is coupled to the tether distal end. An optical camera, having a field of view, is coupled to the camera head, for generating image data. A camera head position sensing system inferentially determines three dimension (3D) position of the camera head and generating inferred camera head position data. A controller is coupled to the camera scope optical camera and the camera head positioning system, for correlating the image and position data. Various embodiments of the positioning system include: (i) an inertial sensor, for correlating camera head movement with inferred camera head 3D position; (ii) a contactless remote position tracking system including a wireless positioning transmitter coupled to the camera head, for transmitting a positional signal and a wireless positioning system receiver for receiving the positional signal, locating the positioning transmitter's 3D position and correlating the positioning transmitter's located position with inferred camera head 3D position; (iii) a remote tether insertion depth sensing system including tether markers arrayed along the tether length and a transceiver coupled in proximity to a rotating machine cavity that is capable of detecting the markers, for correlating a detected marker with inferred camera head 3D position; and (iv) a tether flexure sensing system for correlating sensed tether flexure with inferred camera head 3D position. Some embodiments of the tether flexure sensing system comprises a sensing array coupled to the tether that correlates array distortion with tether flexure, such as a magnetic- or capacitance-based proximity sensor array.

Other embodiments of the invention feature a flexible, position tracking camera scope apparatus, comprising a flexible elongated tether, having a distal end adapted for insertion into a blind cavity of a rotating machine. A camera head is coupled to the tether distal end, which includes therein an optical camera, having a field of view, for generating image data. A camera head position sensing system inferentially determines three dimension (3D) position of the camera head and generates inferred camera head position data.

Additional embodiments of the invention feature a method for internal inspection of rotating machinery, by providing a flexible, position tracking camera scope inspection system. The inspection system includes a camera scope with a flexible elongated tether. The tether has a distal end adapted for insertion into a blind cavity of a rotating machine. A camera head is coupled to the tether distal end and incorporates an optical camera, having a field of view, coupled to the camera head, for generating image data. A camera head position sensing system inferentially determining three dimension (3D) position of the camera head and generates inferred camera head position data. A controller is coupled to the camera scope optical camera and the camera head positioning system, for correlating the image and position data. The featured method is performed by inserting the camera scope into a blind cavity of a power generation machine. The tether and camera head are maneuvered through the rotating machine cavity. The camera and position sensing system respectively capture image and position data. The controller correlates captured image and position data and uses the correlated data to generate an inspection data set. The inspection data set is available for analysis and image manipulation, including composite image generation.

The respective objects and features of the invention may be applied jointly or severally in any combination or subcombination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in a camera scope inspection system with a flexible, tether mounted camera head that is maneuverable in confined internal cavities of power generation machinery. A camera head position sensing system inferentially determines the three dimension (3D) position of the camera head within the inspected machinery. Camera head position data are correlated with camera image data by a controller. In this manner correlated internal inspection image data and corresponding position data are available for future analysis and image tracking.

Figure 1:
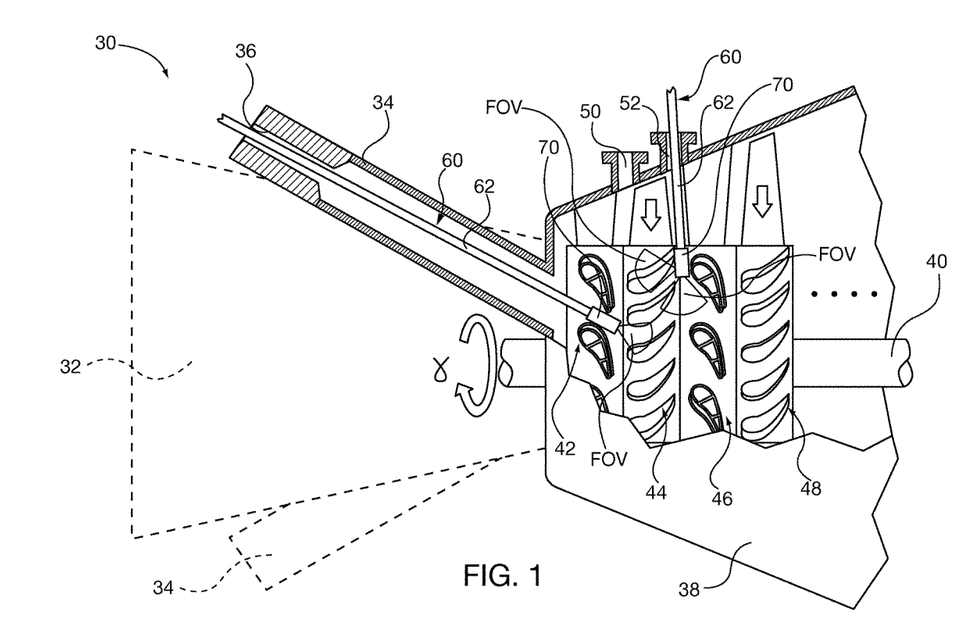
FIG. 1 is a partial cross sectional schematic view of a gas turbine; that is being inspected with two exemplary camera scopes that incorporate embodiments of the invention.
Figure 2:
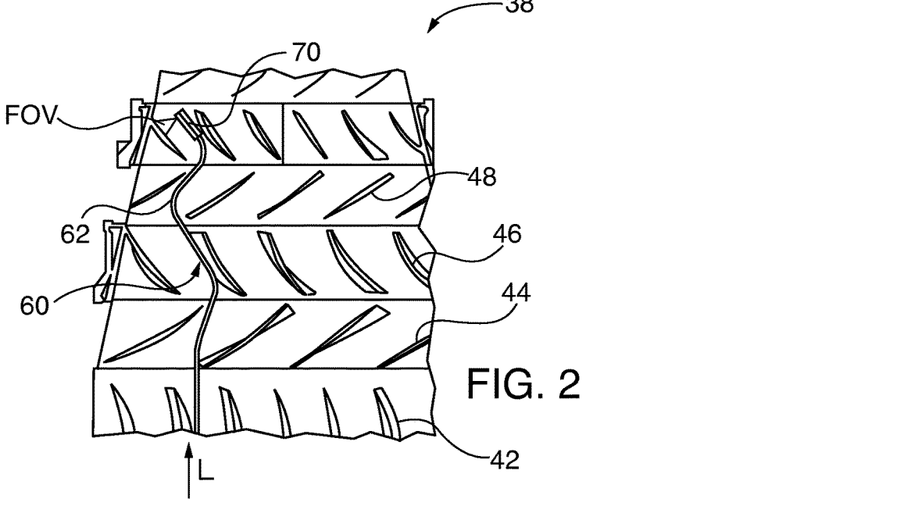
FIG. 2 is a fragmented plan view of a gas turbine engine turbine section showing positioning of an exemplary camera scope of the invention between successive vane and blade rows.
Figure 3:
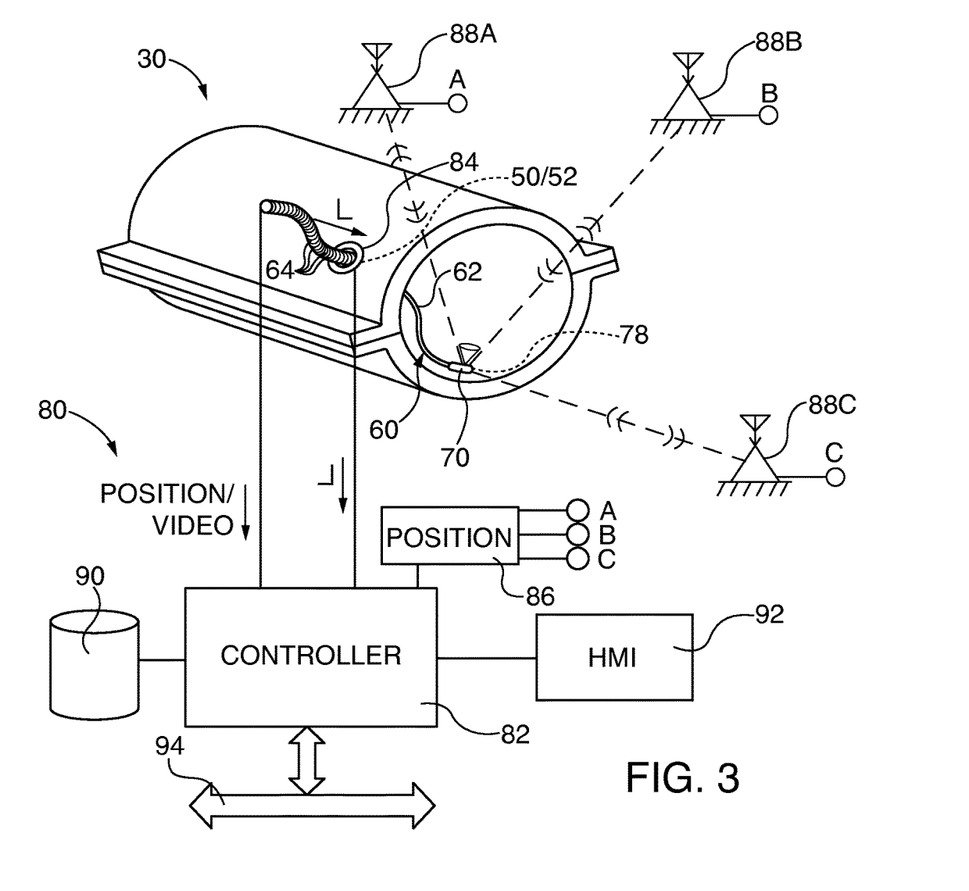
FIG. 3 is a schematic view of a flexible, position tracking camera scope inspection system embodiment being used to perform an inspection within a gas turbine engine casing, wherein a remote tether insertion depth sensing system senses tether insertion L into the casing.

Referring to FIGS. 1-3, embodiments of the invention facilitate automated off-line remote visual inspection of gas turbine 30 internal components, including the compressor section 32, the combustor section 34, the turbine section 38 Row 1 and Row 2 fixed vanes 42, 46; leading Row 1 and Row 2 rotating blades 44, 48 that circumscribe the turbine shaft 40; and ring segments. Embodiments of the present invention flexible tether camera inspection system enables inspection of offline turbines by introducing one or more remote, manually positioned and/or actuated optical camera inspection scopes 60 into one or more of the turbine inspection ports 36, 50 and 52, simultaneously or sequentially. Upon insertion of an inspection scope 60, its tether 62 is selectively positioned manually by an operator or with assistance of an insertion drive mechanism (not shown). One or more cameras are mounted in camera head 70 and image data in each camera's field of view (FOV) are acquired, captured, and if desired archived for further analysis.

The inspection scope 60 is part of the position tracking inspection system 80 that also incorporates a camera head position sensing system for inferentially determining three dimension (3D) position of the camera head 70 and for generating inferred camera head position data. Exemplary embodiments of camera head positioning systems are shown in FIG. 3. Inspection system controller 82 is coupled to the camera scope optical camera, in order to receive and process image data, such as is described in the aforementioned United States patent application publications numbers 2013/0335530 and 2013/019235. The controller 82 is also coupled to the camera head positioning system, for receiving and processing camera head 70 position data and for correlating the image and position data, such as in an inspection data set.

One exemplary camera head position sensing system shown in FIG. 3 is a remote tether insertion depth sensing system including tether markers or sensors 64 that are arrayed along the tether length and a transceiver 84 (e.g., an electromagnetic inductive or capacitive sensor coil or RFID sensor) that is coupled in proximity to a rotating machine cavity 50/52. The transceiver 84 detects the markers 64, which are correlated to the insertion length L of the tether 62 within the cavity 50/52. Tether 62 insertion length L becomes one parameter used by the controller for correlating a detected marker with inferred camera head 3D position.

Another exemplary camera head position sensing system shown in FIG. 3 is a contactless remote position tracking system, which includes a wireless positioning transmitter 78 that is coupled to the camera head 70, for transmitting a positional signal and at least one wireless positioning system receiver/controller that is coupled to the controller 82, for receiving the positional signal, locating the positioning transmitter's 3D position and correlating the positioning transmitter's located position with inferred camera head 3D position. The contactless remote position tracking system shown in FIG. 3 has three receivers 88A, 88B and 88C that are coupled to a wireless positioning system controller 86. Together the receivers/controller system triangulate the transmitter 78 position in three dimensions within the turbine 30 internal cavity and generate camera head 70 position data that are used by the controller 80, along with the image data to in turn generate the inspection data. While separate inspection system controller 80 and position tracking system controller 86 are shown as separate devices in FIG. 3, their functions may be consolidated in or further distributed to other known types of industrial controller or general computing devices, such as personal computers or tablet computers.

Optionally the inspection system controller 82 is in communication with one or more inspection data storage devices 90 or one or more human machine interfaces (HMI) 92. Optionally the controller is in communication with other inspection systems or remote data storage systems via a data bus 94 or other known communications pathway.

Figure 4:
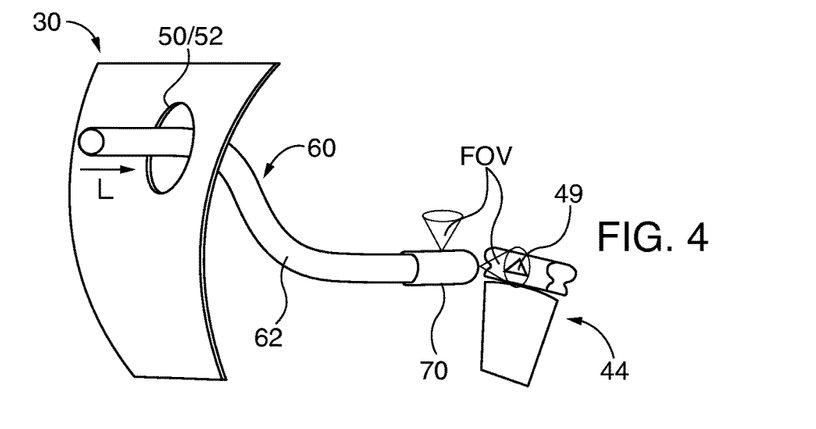
FIG. 4 is a schematic view of a flexible, position tracking camera scope inspection system embodiment being used to perform an inspection within a gas turbine engine casing, wherein designated waypoint markings or objects in an inspected power generation machine viewed by the optical camera field of view are used to corroborate correlation of the image and camera position data by comparison with a previously validated correlation image and position data sets.

The inspection system embodiment of FIG. 4 also incorporates designated waypoint marking recognition capability, such as by placement of indicia markings 49 within the engine 30 that are imaged by the camera system in the camera head 70. Orientation and size of the indicia markings 49 in the camera FOV captured images are used by the inspection system to infer orientation of the camera head and optionally to corroborate correlation of image and camera position data acquired from other inferred camera head positioning system embodiments. Inspection data sets acquired by one camera head positioning system embodiment can be compared with a known, control data set obtained by waypoint marking orientation/size observation or a prior mapping of camera head positions within the turbine engine 30.

Figure 5:
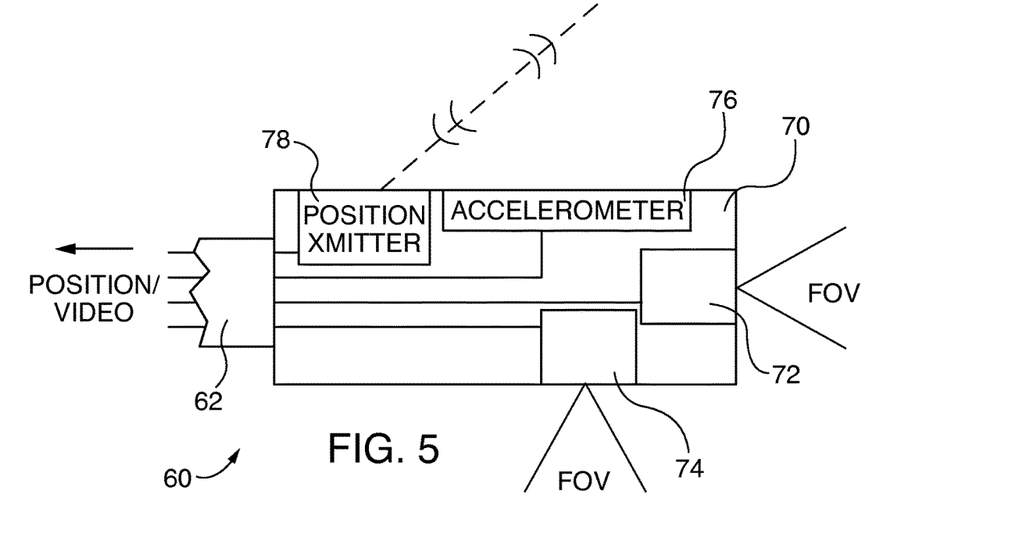
FIG. 5 is a schematic view of an exemplary camera head embodiment of the invention.

FIG. 5 shows an exemplary camera head 70 that includes first and second optical cameras 72, 74 having fields of view (FOV). The camera head 70 is configured to house camera head position sensing system components, such as the wireless position transmitter 78 that was previously described. Another alternative embodiment of a camera head position sensing system incorporates an accelerometer 76 with an inertial sensor, for correlating camera head movement with inferred camera head 3D position. Various configurations of camera heads 70 are shown and described in the aforementioned United States patent application publications numbers 2013/0335530 and 2013/0192353. The camera head 70 is selectively coupled to the tether 62 and different configurations of camera heads may be substituted for different types of machinery inspections.

Figure 6:
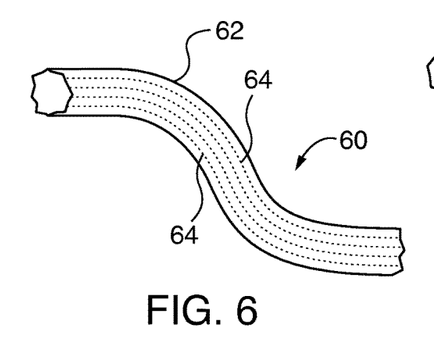
FIG. 6 is a schematic perspective view of an inspection scope tether embodiment of the invention that incorporates a tether flexure sensing system array of sensors oriented axially and radially about the tether circumference, for correlating sensed tether flexure with inferred camera head 3D position.
Figure 7:
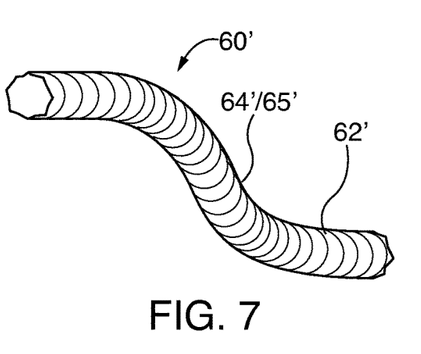
FIG. 7 is a schematic perspective view of another inspection scope tether embodiment of the invention that incorporates a tether flexure sensing system helical array of sensors for correlating sensed tether flexure with inferred camera head 3D position.
Figure 8:
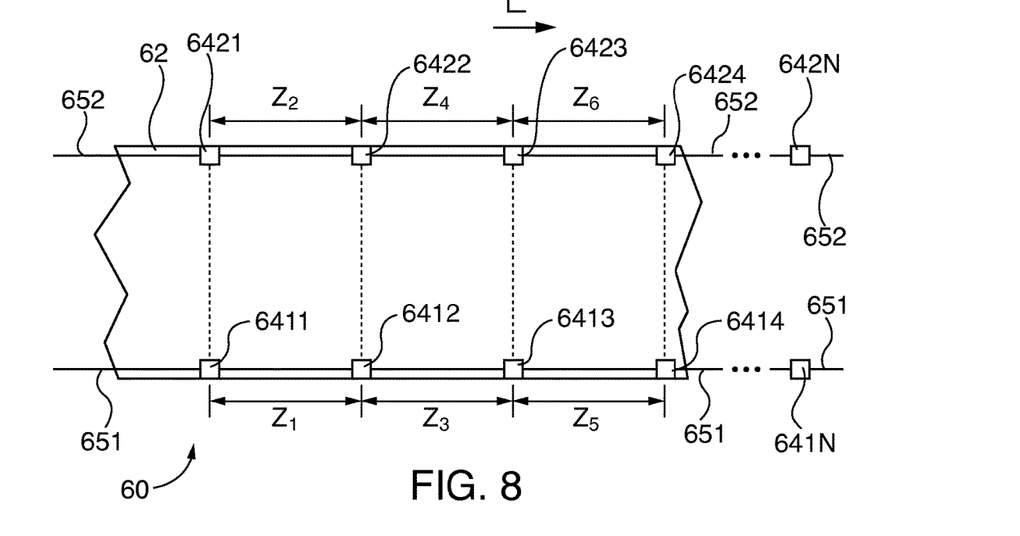
FIG. 8 is a schematic view of the sensor array embodiment of FIG. 6 where the tether is in a straightened, axially extended orientation.
Figure 9:
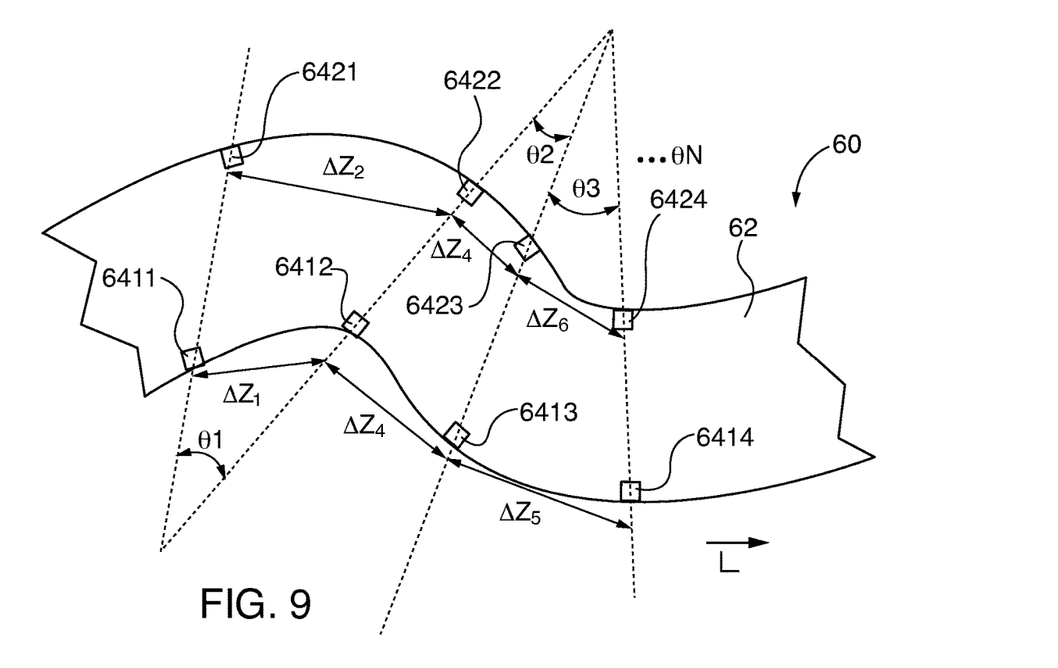
FIG. 9 a schematic view of the sensor array embodiment of FIG. 6 where the tether is flexed.

Other camera head position sensing embodiments, which incorporate tether 62 flexure sensing systems for correlating sensed tether flexure with inferred camera head 3D position, are shown in 6-9. In FIGS. 6 and 8 a sensing array of discrete sensors 64 are oriented radially and axially about or embedded within an outer skin of the tether 62. As shown in FIG. 8, axially and radially aligned rows of sensors, such as sensors 641 1-641N are coupled by a common sensor data lead 651 and an opposed pair of equally spaced sensors 6421-642N are coupled by a common sensor data lead 652. Sensors 64XX along a lead are spaced axially at distance $Z_X$, where X is an integer from 1–N. Comparing FIGS. 8 and 9, tether 62 flexure changes distance ΔZ between sensor pairs. Sensed change in distance ΔZ is correlated with tether 62 flexure, as is denoted by the angular references θN. Tether 62 flexure shape is in turn correlated with the camera head 70 3D orientation within the turbine engine 30 internal cavity. In FIG. 7 the sensor array 64'/65' in the camera scope 60' is oriented helically about or within the tether 62'.

In some embodiments the tether sensors 64/64' comprise magnetic or capacitance proximity sensors that correlate change in proximity between sensors with tether flexure, as shown in FIGS. 6-9. Alternatively the sensor array 64 may comprise an optical position and/or shape sensing system that determines changes in optical length of a multi-core optical fiber, such as referred to in United States patent application publication number 2011/0109898.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A flexible, position tracking camera scope inspection system for internal inspection of power generation machinery, comprising:
a camera scope including:
a flexible elongated tether that is bendable along a tether axial central axis thereof, having axial length, and a distal end for insertion into a blind cavity of a power generation machine;
a flexible, linear sensor array, having a sensor array linear central axis, coupled to and oriented along axial length of the tether, for sensing axial location and radius of bends in the tether along the axial central axis thereof, based on linear distortion of said sensor array along its sensor array linear central axis;
a tether flexure sensing system, coupled to the flexible linear sensor array, for determining profile of the tether along its tether axial central axis, based on axial location and radius of bends sensed by the sensor array;
a camera head coupled to the tether distal end;
an optical camera, having a field of view, coupled to the camera head, for generating image data;
a camera head position sensing system, coupled to the tether flexure sensing system, for inferentially determining three dimension (3D) position of the camera head and for generating inferred camera head position data, based on profile of the tether along its tether axial central axis, that was determined by the tether flexure sensing system; and
a controller coupled to the camera scope optical camera and the camera position sensing system, for correlating the image and position data,
the camera head position sensing system further comprising designated waypoint markings or objects in an inspected power generation machine viewed by the optical camera that are used by the controller to corroborate correlation of the image and camera position data by comparison with a previously validated correlation image and position data set.

2. The system of claim 1, the camera head position sensing system further comprising an inertial sensor coupled to the camera head, for correlating camera head movement with inferred camera head 3D position.

3. The system of claim 1, the camera head position sensing system further comprising a contactless remote position tracking system including a wireless positioning transmitter coupled to the camera head, for transmitting a positional signal and a wireless positioning system receiver for receiving the positional signal, locating the positioning transmitter's 3D position and correlating the positioning transmitter's located position with inferred camera head 3D position.

4. The system of claim 1, the camera head position sensing system further comprising a remote tether insertion depth sensing system including tether markers arrayed along the tether length and a transceiver coupled in proximity to a rotating machine cavity that is capable of detecting the markers, for correlating a detected marker with inferred camera head 3D position.

5. The system of claim 1, the sensor array comprising at least one multi-core optical fiber, which senses axial location and radius of bends in the tether based on changes in optical length of one or more individual fibers in said multi-core optical fiber.

6. The system of claim 1, the sensor array coupled to the tether parallel to or helically oriented about the tether axial central axis that correlates array distortion with tether flexure bends.

7. The system of claim 6, the comprising proximity sensors coupled to the tether that correlate change in proximity between sensors with tether flexure bends.

8. The system of claim 7 the proximity sensors comprising magnetic proximity sensors.

9. The system of claim 7, the proximity sensors comprising capacitance proximity sensors.

10. A flexible, position tracking camera scope apparatus, comprising:
a flexible elongated tether that is bendable along a tether axial central axis thereof, having axial length, and a distal end for insertion into a blind cavity of a power generation machine;
a flexible, linear sensor array, having a sensor array linear central axis, coupled to and oriented along axial length of the tether, for sensing axial location and radius of flexure bends in the tether along the axial central axis thereof, based on linear distortion of said sensor array along its sensor array linear central axis;
a tether flexure sensing system, coupled to the flexible linear sensor array, for determining profile of the tether along its tether axial central axis, based on axial location and radius of bends sensed by the sensor array;
a camera head coupled to the tether distal end;
an optical camera, having a field of view, coupled to the camera head, for generating image data; and
a camera head position sensing system, coupled to the tether flexure sensing system, for inferentially determining three dimension (3D) position of the camera head and for generating inferred camera head position data, based on profile of the tether along its tether axial central axis that was determined by the tether flexure sensing system, the camera head position sensing system further comprising designated waypoint markings or objects in an inspected rotating machine viewed by the optical camera that are used by apparatus to corroborate correlation of the image and camera position data.

11. The apparatus of claim 10, further comprising the camera head position sensing system selected from the group consisting of an inertial sensor, a contactless remote position tracking system, and a remote tether insertion depth sensing system.

12. A method for internal inspection of power generation machine, comprising:
providing a flexible, position tracking camera scope inspection system, having:
a camera scope including:
a flexible elongated tether that is bendable along a tether axial central axis thereof, having axial length, and a distal end adapted for insertion into a blind cavity of a power generation machine;
a flexible, linear sensor array, having a sensor array linear central axis, coupled to and oriented along axial length of the tether, for sensing axial location and radius of flexure bends in the tether along the axial central axis thereof, based on linear distortion of said sensor array along its sensor array linear central axis;
a tether flexure sensing system, coupled to the flexible linear sensor array, for determining profile of the tether along its tether axial central axis, based on axial location and radius of bends sensed by the sensor array;
a camera head coupled to the tether distal end;
an optical camera, having a field of view, coupled to the camera head, for generating image data;
a camera head position sensing system, coupled to the tether flexure sensing system, for inferentially determining three dimension (3D) position of the camera head and for generating inferred camera head position data, based on profile of the tether along its tether axial central axis that was determined by the tether flexure sensing system; and
a controller coupled to the camera scope optical camera and the camera head positioning system, for correlating the image and position data;
inserting the camera head and tether of the camera scope into a blind cavity of a power generation machine;
maneuvering the tether and camera head through the machine cavity, generating images with the camera and generating corresponding position data with the camera head position sensing system;
capturing image and position data, respectively with the camera and the position sensing system;
correlating captured image and position data with the controller; and
generating an inspection data set with the correlated captured image and position data,
designating waypoint markings or objects in an inspected power generation machine that are viewed by the optical camera,
generating image and position data of the waypoint markings or objects;
corroborating with the controller correlation of the generated image and position data of the waypoint markings or objects by comparing them to a previously validated correlation image and position data set.

13. The method of claim 12, further comprising generating inferred camera positioning data with an inertial sensor coupled to the camera head, for correlating camera head movement with inferred camera head 3D position.

14. The method of claim 12, further comprising generating inferred camera positioning data with a contactless remote position tracking system including a wireless positioning transmitter coupled to the camera head, for transmitting a positional signal and a wireless positioning system receiver for receiving the positional signal, locating the positioning transmitter's 3D position and correlating the positioning transmitter's located position with inferred camera head 3D position.

15. The method of claim 12, further comprising generating inferred camera positioning data with a remote tether insertion depth sensing system including tether markers arrayed along the tether length and a transceiver coupled in proximity to a power generation machine cavity that is capable of detecting the markers, for correlating a detected marker with inferred camera head 3D position.

16. The method of claim 12, further comprising generating inferred camera positioning data with a tether flexure sensing system including a sensor array having at least one multi-core optical fiber, which senses axial location and radius of bends in the tether based on changes in optical length of one or more individual fibers in said multi-core optical fiber.

17. The method of claim 12, further comprising generating inferred camera positioning data with a tether flexure sensor array of magnetic or capacitance proximity sensors that that correlate change in proximity between sensors with tether flexure bends.

* * * * *